(12) United States Patent
Vuillemot

(10) Patent No.: US 8,366,445 B2
(45) Date of Patent: Feb. 5, 2013

(54) METHOD FOR DENTAL RESTORATION AND RELATED KIT

(76) Inventor: William C. Vuillemot, DeWitt, MI (US)

( * ) Notice: Subject to any disclaimer, the term of this patent is extended or adjusted under 35 U.S.C. 154(b) by 77 days.

(21) Appl. No.: 12/660,499

(22) Filed: Feb. 26, 2010

(65) Prior Publication Data

US 2011/0212420 A1 Sep. 1, 2011

(51) Int. Cl.
*A61C 5/00* (2006.01)
(52) U.S. Cl. ........... 433/213; 433/223
(58) Field of Classification Search .......... 433/213, 433/223; 700/117
See application file for complete search history.

(56) References Cited

U.S. PATENT DOCUMENTS

| | | | |
|---|---|---|---|
| 3,808,687 A | 5/1974 | Millet | |
| 3,987,545 A | 10/1976 | Kennedy | |
| 4,080,736 A | 3/1978 | Kennedy | |
| 4,129,946 A | 12/1978 | Kennedy | |
| 4,433,959 A * | 2/1984 | Faunce | 433/222.1 |
| 4,695,254 A * | 9/1987 | Herrell | 433/213 |
| 4,775,320 A * | 10/1988 | Marshall et al. | 433/214 |
| 5,027,281 A | 6/1991 | Rekow et al. | |
| 5,192,207 A | 3/1993 | Rosellini | |
| 5,224,049 A * | 6/1993 | Mushabac | 700/163 |
| 5,332,390 A | 7/1994 | Rosellini | |
| 5,378,154 A | 1/1995 | Van Der Zel | |
| 5,452,219 A * | 9/1995 | Dehoff et al. | 700/163 |
| 5,775,913 A | 7/1998 | Updyke et al. | |
| 5,984,682 A | 11/1999 | Carlson | |
| 6,431,871 B1 | 8/2002 | Luthardt | |
| 6,479,592 B2 | 11/2002 | Rheinberger et al. | |
| 6,691,764 B2 * | 2/2004 | Embert et al. | 164/4.1 |
| 6,769,913 B2 | 8/2004 | Hurson | |
| 6,885,464 B1 | 4/2005 | Pfeiffer et al. | |
| 7,010,150 B1 | 3/2006 | Pfeiffer et al. | |
| 7,035,702 B2 | 4/2006 | Jelonek et al. | |
| 7,092,780 B2 * | 8/2006 | Ganley et al. | 700/117 |
| 7,163,443 B2 | 1/2007 | Basler et al. | |
| 7,178,731 B2 | 2/2007 | Basler | |
| 7,217,131 B2 | 5/2007 | Vuillemot | |

(Continued)

OTHER PUBLICATIONS

International Search Report and the Written Opinion of the International Searching Authority, dated Apr. 26, 2011, for Application No. PCT/US11/00345.

(Continued)

*Primary Examiner* — Ralph Lewis
(74) *Attorney, Agent, or Firm* — Butzel Long

(57) ABSTRACT

The disclosure generally relates to a method for forming a dental mold. The method generally includes: (a) scanning an existing dental structure to generate a three-dimensional first digital model of the existing dental structure, (b) modifying the first digital model of the existing dental structure to generate a three-dimensional second digital model of a planned dental structure; (c) generating a three-dimensional third digital model corresponding to a negative of the second digital model; (d) digitally sectioning the third digital model into at least one buccal model portion and at least one lingual model portion of the third digital model; and (e) creating a dental mold comprising at least one buccal mold portion and at least one lingual mold portion based on the sectioned third digital model. The disclosure also relates to (a) methods of assembling the dental mold over a tooth and a gum of a patient having an existing dental structure in need of dental restoration, (b) methods of performing a dental restoration on the existing dental structure of the patient using the dental mold, and (c) kits including components for forming the dental mold and/or for performing the dental restoration using the dental mold.

17 Claims, 11 Drawing Sheets

U.S. PATENT DOCUMENTS

| | | | |
|---|---|---|---|
| 7,220,124 | B2 | 5/2007 | Taub et al. |
| 7,536,234 | B2 | 5/2009 | Kopelman et al. |
| 2002/0064759 | A1 | 5/2002 | Durbin et al. |
| 2002/0076530 | A1 | 6/2002 | MacDougald et al. |
| 2002/0081554 | A1 | 6/2002 | Marshall et al. |
| 2002/0160337 | A1 | 10/2002 | Klein et al. |
| 2003/0069326 | A1 | 4/2003 | Stangel et al. |
| 2004/0167246 | A1 | 8/2004 | Subelka et al. |
| 2004/0197740 | A1 | 10/2004 | Amar |
| 2005/0133955 | A1 | 6/2005 | Christensen |
| 2005/0177261 | A1 | 8/2005 | Durbin et al. |
| 2006/0115792 | A1 | 6/2006 | Vuillemot |
| 2008/0153069 | A1* | 6/2008 | Holzner et al. ............... 433/223 |
| 2009/0023112 | A1 | 1/2009 | Ganley et al. |
| 2009/0130634 | A1 | 5/2009 | Ganley et al. |
| 2010/0219546 | A1* | 9/2010 | Puttler et al. ................... 264/16 |

OTHER PUBLICATIONS

Form PCT/IB/326 Notification Concerning Transmittal of International Preliminary Report on Patentability (Chapter 1 of the Patent Cooperation Treaty), date of mailing: Sep. 7, 2012.

Goldstein, Martin B., "Template-Assisted Direct Composite Veneers," www.dentistrytoday.com, Feb. 2010, 6 pages.

Schoenbaum, Todd R., "Decoding CAD/CAM and Digital Impression Units," www.dentistrytoday.com, Feb. 2010, 5 pages.

Goldstein, Martin B., "Direct Bonded Composite Veneers for the Artistically Challenged Dentist," http://www.smile-vision.net/docs/goldsteinbonding.pdf, 5 pages.

\* cited by examiner

METHOD FOR DENTAL RESTORATION AND RELATED KIT

BACKGROUND OF THE DISCLOSURE

1. Field of the Disclosure

The present disclosure relates generally to dental prosthesis, and more particularly to methods of forming dental prosthesis and method of forming dental molds therefor. The disclosure specifically relates to methods of forming dental prosthesis in situ in a patient's mouth by injection molding using a dental mold of a corrected model of the patient's dentition.

2. Related Art

Diagnostic wax-ups have been used for decades, to study ways of restoring damaged or mal-aligned dentitions. Once solutions are arrived at using the wax-up, a treatment plan is formed. The work in the mouth is made to approximate the wax-up, using various conventional methods. These methods include bonding (applying the restoratives directly in the mouth using a sculpting technique, or "free-hand" technique), crown and bridge preps and placement, or applying orthodontic appliances. These various methods can only approximate the diagnostic wax-up, because the work subsequently provided is subject to the dentist's, and/or dental lab technician's interpretations or hands-on manipulations.

U.S. Pat. No. 3,808,687 to Millet teaches pontics with a rigid core formed of a plastic material such as acrylic, lucite, plexiglass or other hard material, and detachable cap formed of a flexible plastic such as polyethylene which have the external contours of a natural tooth. The external configuration of the cap is substantially the same as the porcelainized portion of the restoration to be formed. The pontics are used for creating an investment mold for casting a metal frame of gold or other suitable materials to which porcelain is applied. The dental restoration is then fit into the patient's mouth.

U.S. Pat. No. 3,987,545 to Kennedy teaches methods for forming a temporary dental prosthesis as a bridge in situ in a patient's mouth for restoration of missing or broken teeth. The method utilizes a positive model of the patient's mouth which is corrected to the desired size and shape of the teeth to be restored. An elastomeric mold is formed using the model as a pattern which is fitted over the patient's jaw. A self-curing liquid resin is drawn into the cavity by vacuum across the bridge to form the dental prosthesis which is removed and then cemented in place. This requires that a good seal be provided between the jaw and the mold.

U.S. Pat. No. 4,080,736 also to Kennedy teaches a method and apparatus for forming a dental prosthesis for restoration of a patient's teeth. An elastomeric mold and a hard model are secured together to form an assembly with a mold cavity within. The assembly is placed in a vacuum chamber to produce a vacuum inside the chamber and the mold. When a connection between a source and the assembly is opened a liquid material is pushed into the mold cavity to form the prosthesis, which is then installed in the patient.

U.S. Pat. No. 4,129,946 to Kennedy teaches hollow dental crown forms, preferably co-polyester plastics, having the shape of a natural tooth for holding and shaping composite resin material applied to a tooth which requires restoration. A tab which provides a gripping handle is formed at the base of the crown form, and a flange is formed around the base of the crown form. The crown is then installed in the patient.

U.S. Pat. Nos. 5,192,207 and 5,332,390 to Rosellini teach crowns or replacement teeth and methods of production thereof. The crown or replacement teeth are formed by filling a transparent shell tooth with a light setting resin and disposing the filled transparent shell tooth onto a prepared tooth of a patient. The filled shell tooth is illuminated to set the resin and bond it to the shell tooth form. Polishing and shaping are then done in situ to form the crown.

U.S. Pat. No. 5,775,913 to Updyke et al. teach a method of making caps of eight different sizes for each of a persons teeth. The caps are preferably prepared from quartz or silicon dioxide filled acrylic materials. The caps can be placed over a prepared tooth and exposed to ultraviolet light to form the solid capped tooth.

U.S. Pat. No. 5,984,682 to Carlson teaches permanent composite dental bridges constructed either in situ or ex situ. The material is applied in the in situ process between abutment teeth and wings formed from the composite material are attached to surfaces of the abutment teeth before curing. These steps are successively repeated until a dental bridge is form within the patient's mouth. A gingival stent is used as a platform upon which the composite laminations are formed, and is removed after the formation of the bridge prior to contouring and finishing of the bridge.

U.S. Pat. No. 6,769,913 to Hurson discloses an impression cap and methods of taking dental impressions in a patient's mouth by injecting an impression material into an inner cavity of the impression cap. The impression cap is then removed from the patient's mouth for the fabrication of a dental restoration.

U.S. Pat. No. 7,217,131 to Vuillemot relates to a method and kit for dental restoration. An integral mold for forming a dental prosthesis is formed by taking an impression of existing teeth, preparing a model of the existing teeth, preparing a waxed-up model of a planned restoration of the existing teeth, and preparing the integral mold from the waxed-up model.

Objects

Therefore, it is an object of the present disclosure to provide an improved method of forming a dental mold and of forming a dental prosthesis using the dental mold in situ in a patient's mouth by injection molding. It is further an object of the present disclosure to provide a kit of materials, supplies and instructions for forming the dental mold and for correcting the teeth of a patient by the provided methods.

These and other objects may become increasing apparent by reference to the following description.

SUMMARY

The present disclosure generally relates to a method for forming a dental mold. In other embodiments, the disclosure also relates to (a) methods of assembling the dental mold over a tooth and a gum of a patient having an existing dental structure in need of dental restoration, (b) methods of performing a dental restoration on the existing dental structure of the patient using the dental mold, and (c) kits including components for forming the dental mold and/or for performing the dental restoration using the dental mold.

A first aspect of the disclosure relates to a method for forming a dental mold. The method generally includes: (a) scanning an existing dental structure to generate a three-dimensional first digital model of the existing dental structure; (b) modifying the first digital model of the existing dental structure to generate a three-dimensional second digital model of a planned dental structure, the planned dental structure having spatial surface contours different from those of the existing dental structure; (c) generating a three-dimensional third digital model corresponding to a negative of the second digital model, wherein (i) the third digital model comprises a solid volume corresponding to walls of the eventual dental mold, and (ii) the solid volume defines a void volume corresponding to the planned dental structure; (d) digitally sectioning the solid volume of the third digital model into two or more sub-volumes, thereby defining at least one buccal model portion of the third digital model and at least one lingual model portion of the third digital model such that the buccal model portion and the lingual model portion share at least one common interfacial surface in the third digital model; (e) creating a dental mold comprising at least one buccal mold portion and at least one lingual mold portion, wherein (i) the buccal mold portion has a shape corresponding to the buccal model portion; (ii) the lingual mold portion has a shape corresponding to the lingual model portion; and (iii) the buccal mold portion and the lingual mold portion are separate structures that together define a void volume corresponding to the planned dental structure when assembled; and (f) optionally adding at least one inlet port and at least one outlet port to the dental mold such that, when the dental mold is assembled, the inlet port and the outlet port (i) are in fluid communication with each other via the void volume defined by the assembled dental mold and (ii) are individually in fluid communication with a volume external to the assembled dental mold.

In another embodiment, a method for forming a dental mold generally includes: (a) providing (e.g., to a dental CAD/CAM system) a three-dimensional digital model corresponding to a negative of a planned dental structure (e.g., a digital model generated according to the foregoing methods or provided as a digital input to a computer or dental CAD/CAM system), the planned dental structure having spatial surface contours different from those of an existing dental structure of a patient in need of dental restoration, wherein (i) the digital model comprises a solid volume corresponding to walls of the eventual dental mold, and (ii) the solid volume defines a void volume corresponding to the planned dental structure; (b) digitally sectioning the solid volume of the digital model into two or more sub-volumes, thereby defining at least one buccal model portion of the digital model and at least one lingual model portion of the digital model such that the buccal model portion and the lingual model portion share at least one common interfacial surface in the digital model; (c) creating a dental mold comprising at least one buccal mold portion and at least one lingual mold portion, wherein (i) the buccal mold portion has a shape corresponding to the buccal model portion; (ii) the lingual mold portion has a shape corresponding to the lingual model portion; and (iii) the buccal mold portion and the lingual mold portion are separate structures that together define a void volume corresponding to the planned dental structure when assembled; and (d) optionally adding at least one inlet port and at least one outlet port to the dental mold such that, when the dental mold is assembled, the inlet port and the outlet port (i) are in fluid communication with each other via the void volume defined by the assembled dental mold and (ii) are individually in fluid communication with a volume external to the assembled dental mold. In an embodiment, the three-dimensional digital model can be provided in a form that is already digitally sectioned into the sub-volumes such that the method for forming the physical dental mold can more generally include a first step of providing the digitally sectioned three-dimensional digital model and a second step of creating the dental mold as described above.

Various refinements to the dental mold formation methods are possible. For example, the dental structure can comprise at least one tooth and neighboring gum portion of a patient in need of dental restoration, or the dental structure can comprises an entire dental arch and neighboring gum portion of a patient in need of dental restoration. In either case, the planned dental structure suitably is consistent with a planned dental restoration procedure selected from the group consisting of fractured tooth repair, decayed tooth repair, worn tooth repair, discolored tooth masking, tooth reshaping, tooth repositioning, tooth rotation, tooth replacement, and combinations thereof. The digital sectioning in part (d) can comprise defining two or more buccal model portions and two or more lingual model portions of the third digital model such that (i) each buccal model portion shares at least one common interfacial surface with at least one lingual model portion in the third digital model, (ii) each buccal model portion shares at least one common interfacial surface with at least one other buccal model portion in the third digital model, (iii) each lingual model portion shares at least one common interfacial surface with at least one buccal model portion in the third digital model, and (iv) each lingual model portion shares at least one common interfacial surface with at least one other lingual model portion in the third digital model. For example, the buccal model portions and the lingual model portions can together correspond to an entire dental arch of the planned dental structure. In an embodiment, the common interfacial surface defines complementary alignment structure between the buccal model portion and the lingual model portion of the third digital model, for example an irregular interface for facilitating the proper alignment of the eventual mold portions during assembly of the dental mold and for limiting slippage of the mold portions in the assembled dental mold (e.g., complementary mating structures such as rods/holes and/or ribs/grooves). Suitably, the buccal mold portion and the lingual mold portion comprise a transparent, rigid polymeric material (e.g., a thermoplastic acrylic polymer such as poly(methymethacrylate)). At least one of the buccal mold portion and the lingual mold portion can comprise an internal heating element. Suitably, the dental mold in part (e) is formed by: (i) mounting a mold blank onto a substrate holder of a computer numerically controlled (CNC) machining apparatus; (ii) performing a CNC machining process based on the buccal model portion of the third digital model, thereby forming the corresponding buccal mold portion from the mold blank; and (iii) repeating the foregoing parts (i) and (ii) for each of the buccal and lingual model portions in the third digital model, thereby forming each of the corresponding buccal and lingual mold portions of the dental mold.

Another aspect of the disclosure relates to a method of assembling a dental mold over a tooth and a gum of a patient having an existing dental structure in need of dental restoration to a planned dental structure. The method generally includes: (a) providing the dental mold according to any of the foregoing embodiments (e.g., as formed by any of the foregoing methods), wherein the buccal mold portion and the lingual mold portion of the dental mold correspond to the planned dental structure of the patient (e.g., the buccal mold portion and the lingual mold portion are separate structures that together define a void volume corresponding to the planned dental structure when assembled at a common interfacial surface, the planned dental structure having spatial surface contours different from those of the existing dental structure of the patient); (b) seating at least a portion of the buccal mold portion against a buccal side of the patient's gum or tooth; (c) seating at least a portion of the lingual mold portion against a lingual side of the patient's gum or tooth; (d) contacting the buccal mold portion and the lingual mold portion at their common interfacial surface; and (e) securing the buccal mold portion and the lingual mold portion in place, thereby assembling the dental mold in a sealed configuration over the tooth and the gum of the patient, the sealed configuration defining a closed space between the dental mold and the existing dental structure. In a refinement, (i) the buccal mold portion and the lingual mold portion comprise complementary alignment structures at their common interfacial surface; and (ii) contacting the buccal mold portion and the lingual mold portion in part (d) comprises mating the complementary alignment structures. In an embodiment, securing the buccal mold portion and the lingual mold portion in part (e) comprises fitting a clip over adjacent buccal and lingual mold portions.

Another aspect of the disclosure relates to a method of performing a dental restoration with a fluid polymer composition on a patient having an existing dental structure in need of dental restoration to a planned dental structure. The method generally includes: (a) providing the dental mold according to any of the foregoing embodiments (e.g., as formed by any of the foregoing methods), wherein the buccal mold portion and the lingual mold portion of the dental mold correspond to the planned dental structure of the patient (e.g., the buccal mold portion and the lingual mold portion are separate structures that together define a void volume corresponding to the planned dental structure when assembled at a common interfacial surface, the planned dental structure having spatial surface contours different from those of the existing dental structure of the patient); (b) preparing selected teeth to be restored for bonding with the fluid polymer composition; (c) optionally, covering teeth which are not to be restored with a polymer release material (e.g., PTFE, petrolatum, glycerine); (d) fitting the dental mold over the existing dental structure (e.g., by performing any of the foregoing assembly methods), wherein (i) the mold defines a closed space to be filled between teeth of the existing dental structure and the mold, and (ii) the closed space represents the difference between the existing dental structure and the planned dental structure; (e) injection molding via the inlet port a fluid dental restoration polymer composition which is curable on prepared teeth to be restored into the mold to fill the closed space in the mold with the covered teeth and the teeth to be restored; (f) curing the fluid polymer composition (e.g., with light, such as with ultraviolet light ranging from about 465 nm to about 480 nm, and/or with heat) onto the teeth to be restored in the dental mold; and (g) removing the dental mold from the teeth and the polymer release material, if present, from the covered teeth to provide the planned dental structure in the patient.

Various refinements to the dental restoration method are possible. For example, the injection molding in part (e) can further comprise applying a vacuum to the outlet port to facilitate the removal of excess air and excess fluid polymer resulting from the injection molding. The dental restoration fluid polymer composition can be a particle-filled and pigmented poly(acrylicacid)polymer containing a curing agent activated by light. In an embodiment, in part (b) prepared teeth are etched with an acid and then coated with a primer (e.g., alkyl dimethacrylate resins) and bonding agent (e.g., methacrylate ester monomers) for bonding the dental restoration fluid polymer composition to the prepared teeth. Optionally, alternate of the teeth to be restored are restored in two or more repetitions of the parts (b) to (g) of the restoration method. At the end of the restoration method, the exposed surfaces of the restored teeth can be finished Another aspect of the disclosure relates to a kit for forming a dental mold and for performing a dental restoration on a patient with the dental mold. The kit generally includes: (a) a plurality of mold blanks for forming a buccal mold portion or a lingual mold portion of the dental mold; (b) a fluid dental restoration polymer composition curable on teeth to be restored; (c) instructions showing at least one of the formation, assembly, and use of the dental mold according to any of the foregoing embodiments; (d) optionally, a polymer release material; and (e) optionally, an acid etchant for the teeth to be restored, a primer for these teeth and a bonding agent for bonding the fluid polymer composition to these teeth. The mold blanks can have a rectangular prism shape sized for the formation of the dental mold in a human mouth. Alternatively of additionally, the mold blanks can have an arcuate block shape sized for the formation of the dental mold in a human mouth. In an embodiment, the fluid polymer composition comprises particles and pigment in a poly(acrylicacid)polymer composition containing a curing agent activated by light.

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the examples, drawings, and appended claims, with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawing wherein.

Figure 1:
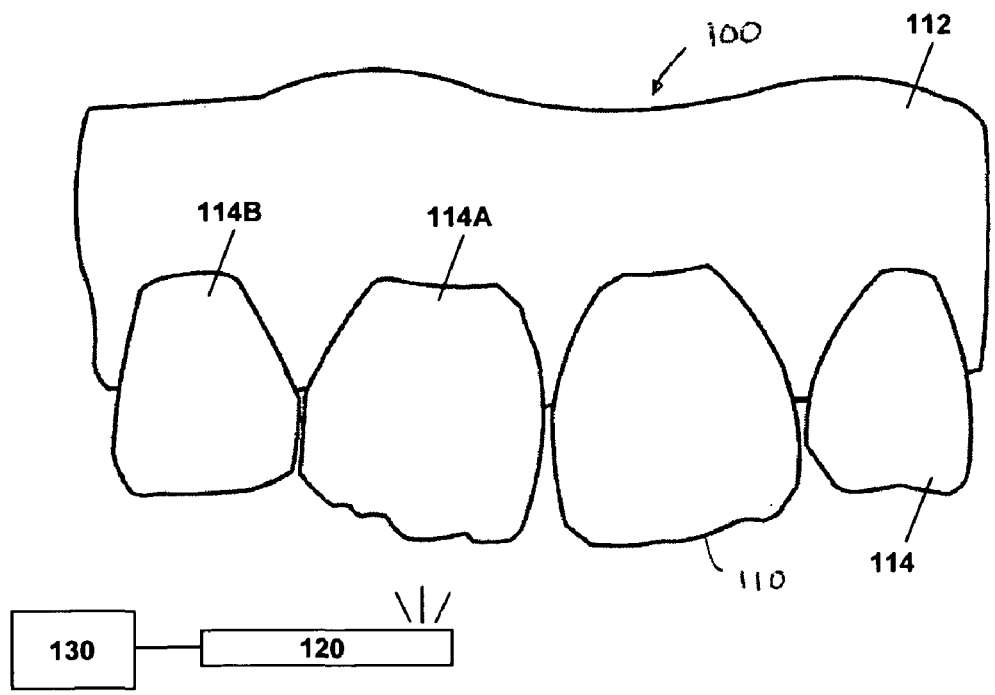
FIG. 1 is an illustration of an existing dental structure 110 (or, equivalently, a first digital model 100 thereof).

While the disclosed apparatus and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The present disclosure generally relates to a method for forming a dental mold. The method generally includes: (a) scanning an existing dental structure to generate a three-dimensional first digital model of the existing dental structure, (b) modifying the first digital model of the existing dental structure to generate a three-dimensional second digital model of a planned dental structure; (c) generating a three-dimensional third digital model corresponding to a negative of the second digital model; (d) digitally sectioning the third digital model into at least one buccal model portion and at least one lingual model portion of the third digital model; and (e) creating a dental mold comprising at least one buccal mold portion and at least one lingual mold portion based on the sectioned third digital model.

In other embodiments, the disclosure also relates to (a) methods of assembling the dental mold over a tooth and a gum of a patient having an existing dental structure in need of dental restoration, (b) methods of performing a dental restoration on the existing dental structure of the patient using the dental mold, and (c) kits including components for forming the dental mold and/or for performing the dental restoration using the dental mold.

An object of the disclosure to provide a dental mold and related method for improving a patient's current dental condition or acquired bite. The current condition, or wants or needs, described by the patient is referred to as the chief complaint. Current condition, or acquired bite, may present as one or more of the following: worn tooth surfaces (when areas which are ideally or normally sharp and pointed are flattened or worn down); fractured teeth; severely decayed teeth; discolored or stained teeth; teeth which are too small for the arches and therefore have excess space between them; and mal-positioned or mal-aligned teeth. Therefore, the desired changes, or restoration of the teeth can be as follows: re-addition of worn surface (which may involve many teeth, and allows the option of "opening the bite"); repair and restoration of fractured teeth; repair and restoration of decayed teeth; replacement of absent or damaged teeth (bridging), covering up of unsightly stains or discolorations; widening of small teeth to close spaces or gaps; and additive or subtractive coronoplasty to improve symmetry and alignment (masking of malposed teeth-giving impression of "instant orthodontics"). These and a variety of other conditions can be improved using a dental restoration technique according to the disclosure. Examples include fractures, gaps, wear, and rotations and/or malpositions.

The present disclosure further provides a kit which provides all necessary materials and supplies in a plastic carrying case. The case can be moved from operatory to operatory as needed. The kit also contains all necessary educational materials, including written, video, and CD form for delivery of instruction. The kit provides all necessary contact information for reorder of needed products, and also contacts for technical support.

A "positive model" of a dental structure is a model (either physical or digital) in which each tooth and/or gum portion is represented by a projection or bulge having contours identical in size and shape to a corresponding tooth and/or gum portion. Similarly, a "negative model" of a dental structure is a model (either physical or digital) in which each tooth and/or gum portion is represented by a cavity or recess with contours identical in size, but opposite in shape to the contours of the corresponding tooth and/or gum portion. A "digital model" of a dental structure represents any convenient mathematical description (e.g., point-based, surface-based, and/or volume-based) of the dental structure and is generally stored in a computer system to facilitate various actions on the digital model such as model retrieval, viewing of the model on a display, model manipulation/transformation (e.g., to view potential results of a planned dental restoration), and providing the model as instructions to a computer-aided manufacturing device to form a physical replica of the digital model.

The terms "buccal" and "lingual" are relative spatial terms representing generally opposing sides of a dental structure, whether it is a physical structure or digital model of an existing or planned structure. Buccal refers to the side of the structure generally regarded as the front (i.e., the side that is visible and exposed when the mouth is open), while lingual refers to the side of the structure generally regarded as the back (i.e., the side that is not generally visible even when the mouth is open).

The term "polymer release material" as used herein refers to a material such as a tape for wrapping or draping untreated teeth. The material acts as a parting agent, preventing the molded composite from sticking to a surface covered with the material. The term refers to a material including, but not limited to tape such as a pipe thread tape including polytetrafluoroethylene (PTFE) pipe thread tapes. One example of the polymer release material is TEFLON pipe thread tape (DuPont, Wilmington, Del.). Alternatively, the polymer release material can be a viscous liquid, solid, or semi-solid lubricating agent (e.g., petrolatum (such as VASELINE), glycerine).

The term "fluid polymer composition" as used herein refers to a flowable material which can be cured to harden the material, including dental composite resins. The fluid polymer composition is preferably curable by exposure to light, however chemical curing is within the scope of the invention. Most preferably, the composition is cured with ultraviolet light of about 465 nanometers (nm) to about 480 nm. One example of a composite resin is HELIOMOLAR Flow composite (Ivoclar Vivadent, Amherst, N.Y.) which is a monomer matrix of 2,2-bis-4-(3-methacryloxy-2-hydroxypropoxy)-phenylpropane (Bis-GMA), urethane dimethacrylate and decandiol dimethacrylate (40.5 wt %) with highly dispersed silicon dioxide, ytterbiumtrifluoride and copolymer (59 wt %) fillers and additionally catalysts, stabilizers and pigments (0.5 wt %).

Dental Mold Formation

Figure 2:
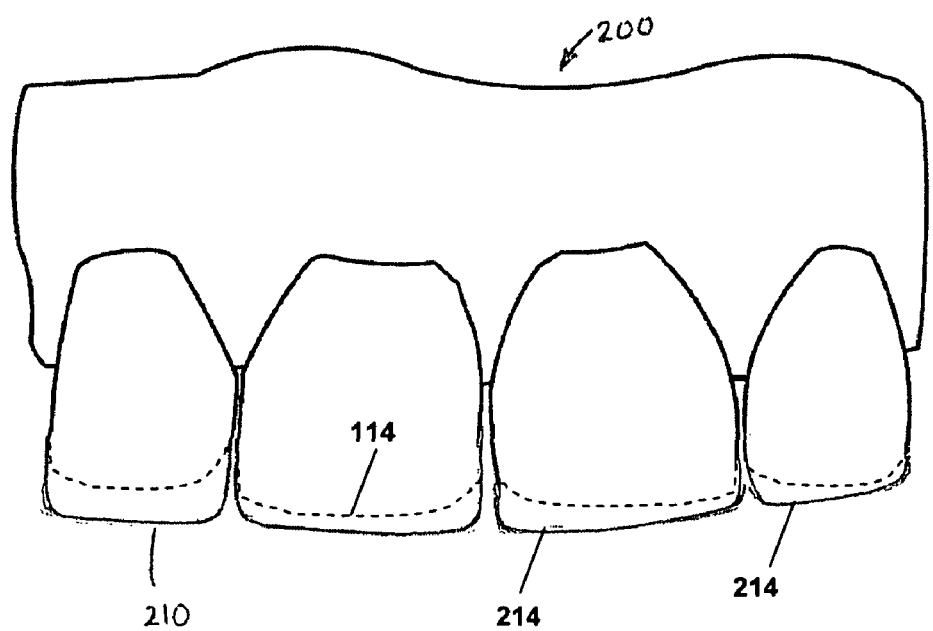
FIG. 2 is an illustration of a second digital model 200 showing a planned dental structure 210.

FIGS. 1-6 illustrate steps in a general method of forming a dental mold according to the disclosure. The method generally includes: (a) scanning an existing dental structure to generate a three-dimensional first digital model of the existing dental structure (FIG. 1), (b) modifying the first digital model of the existing dental structure to generate a three-dimensional second digital model of a planned dental structure (FIG. 2); (c) generating a three-dimensional third digital model corresponding to a negative of the second digital model (FIGS. 3A-3D); (d) digitally sectioning the third digital model into at least one buccal model portion and at least one lingual model portion of the third digital model (FIGS. 4A-4C); (e) creating a dental mold comprising at least one buccal mold portion and at least one lingual mold portion based on the sectioned third digital model (FIGS. 5A-5C and 7); and (f) optionally adding at least one inlet port and at least one outlet port to the dental mold.

FIG. 1 equivalently represents either an existing dental structure 110 (i.e., a physical object) or a first digital model 100 of the existing dental structure 110 (i.e., a digital object stored in a computer-readable medium). The existing dental structure 110 can represent a patient's pre-existing dental structure at any time prior to a planned dental restoration procedure. For example, the existing dental structure 110 can represent the patient's pre-existing dental structure in its natural state prior to visiting a dentist to discuss a planned dental restoration procedure. Alternatively, the existing dental structure 110 can represent the patient's dental structure after one or more pre-restoration dental preparatory procedures (e.g., filing, cutting, buffing, etc. procedures performed before a fluid polymer injection into the eventual dental mold 400). The existing dental structure 110 generally includes at least a portion of a gum 112 and at least one tooth 114 of a patient in need of dental restoration. FIG. 1 shows a segment of a patient's existing dental structure 110, illustrating maxillary central 114A and lateral 114B incisors that have been worn or fractured such that the leading surface of the teeth 114 does not extend as far as desired and does not have an aesthetically pleasing contour. In general, however, the first digital model 100 can be of any subset of a patient's teeth that is in need of dental restoration, for example including one or more incisors or canines (e.g., where cosmetic or functional restorations such as discolored tooth masking, tooth reshaping, repositioning, veneer formation, etc. are desired) and/or one or more molars or premolars (e.g., where cosmetic or functional restorations such as discolored tooth masking, crown formation, inlay formation, overlay formation, etc. are desired) on either or both of the upper arch or lower arch. In an embodiment, the dental structure can include an entire dental arch and neighboring gum portion of a patient (e.g., entire upper arch, entire lower arch, or entire upper and lower arches).

The scanning can be performed by any conventional optical scanner capable scanning a physical surface and converting the three-dimensional contour data of the scanned physical surface into a three-dimensional digital model of the physical surface. For example, commercially available dental imaging units (DIUs) or dental CAD/CAM systems capable of scanning an existing dental structure (e.g., as video or a series of single images) and converting the same to a three-dimensional data file representing the dental structure. In the context the present disclosure, the scanned physical surface is the existing dental structure 110 along with its component gum 112 and teeth 114, and the optical scanner preferably is able to resolve spatial variations on a physical length scale appropriate for human teeth (e.g., a size resolution on a scale ranging down to at least 1 μm, 2 μm, 5 μm, 10 μm, 20 μm, or 50 μm). In an embodiment, the dental structure 110 is pretreated with a non-reflective substance (e.g., a sprayed powder or liquid) to enhance the imaging capability of the scanner. As shown in FIG. 1, the optical scanner can be an intraoral scanner 120 incorporating a light that illuminates dental structure 110 as images and three-dimensional contour data are acquired. Suitably, the scanner 120 is electronically connected to a computer system 130 (e.g., a dental CAD/CAM system) that stores the scanned data as they are acquired. Individual, overlapping scanned image segments of the existing dental structure can be assembled by the computer system 130 to form a composite set of three-dimensional contours that represents the first digital model 100 of the dental structure 110 that is stored in the computer system 130. Representative apparatus and methods for scanning the existing dental structure 110 and forming the resulting first digital model 100 of the same (e.g., including the assembly of component images) are described in U.S. Publication No. 2002/0064759, U.S. Pat. No. 6,885,464, and U.S. Pat. No. 7,010,150, incorporated herein by reference. A suitable commercial dental CAD/CAM system is the CEREC system available from Sirona Dental Systems, Inc. (Long Island City, N.Y.), which system includes a BLUECAM optical scanner for image acquisition, an OPTISPRAY pretreatment spray for providing a non-reflective surface to the teeth, and a CEREC 3D software system that stores scanned images and builds the first digital model. Other suitable commercial dental DIU and CAD/CAM systems are available, for example from Sullivan-Schein Dental, Inc. (E4D DENTIST system from D4D Technologies using a 3-angle laser image capture device), 3M ESPE (LAVA C.O.S. system using a LED-illuminated digital video wand to capture and digitize the dental structure), and Cadent (ITERO system using a parallel confocal imaging laser to capture dental structure data).

FIG. 2 illustrates a three-dimensional second digital model 200 of a planned dental structure 210. The second digital model 200 is formed by modifying the first digital model 100 of the existing dental structure 110. As a result, the planned dental structure 210 has spatial surface contours different from those of the existing dental structure 110. Suitably, the planned dental structure 210 is consistent with any desired planned dental restoration, whether cosmetic or functional, for example including fractured tooth repair, decayed tooth repair, worn tooth repair, discolored tooth masking, tooth reshaping, tooth repositioning, and/or tooth rotation. More specific examples include veneer, crown, inlay, or overlay formation. Different restorative techniques can be combined as desired within a given planned dental structure 210 (e.g., a cosmetic restoration for incisors and canines combined with a functional restoration for selected molars or premolars). As specifically illustrated in FIG. 2, the planned dental restoration includes the extension and smoothing of the leading edge of the existing incisors 114 (illustrated by the dotted line) to have a desired result illustrated by planned incisors 214 that have a smoother, extended leading edge.

The first digital model 100 can be modified by any convenient means to form the second digital model 200. Generally, the dental CAD/CAM system 130 facilitates the formation of the second digital model 200 by a dental professional using the interface of the system 130. Commercial dental CAD/

CAM systems typically include a database containing a variety of common morphologies for human teeth and are capable of suggesting a proposed planned dental structure 210 based on such morphologies and the existing dental structure 110. The dental professional can select a proposed dental structure, manually edit a proposed dental structure, and/or manually edit the first digital model 100 to arrive at the second digital model 200 of the planned dental structure 210. A suitable commercial dental CAD/CAM system for forming the second digital model 200 includes the CEREC system mentioned above.

FIGS. 3A-D illustrate a three-dimensional third digital model 300 that corresponds to a negative of the second digital model 200. As shown in the figures, the first and second digital models 100, 200 are positive models of the existing and planned dental structures 110, 210 respectively, and the third digital model 300 is a negative model of the planned dental structure 210. Given an approximate thickness T (representatively shown in FIG. 3D), the second digital model 200 can be digitally manipulated to form the corresponding third digital model 300 as a negative according to known mathematical/computational procedures, for example as disclosed in U.S. Pat. No. 7,220,124, incorporated herein by reference. The approximate thickness T of the third digital model 300 represents an average distance from an internal surface of the model 300 (i.e., which defines the boundary of the planned dental structure 210) and to an external surface of the model 300 (which corresponds to an external surface of the eventual dental mold). The thickness T need not be uniform throughout the third digital model 300 and can have any convenient value to facilitate the comfortable placement of the eventual dental mold in a patient's mouth. However, the thickness T should be large enough to provide structural integrity to the dental mold and a good seal over the patient's gum and teeth once inserted. Suitably, the thickness T can range from 1 mm to 10 mm at various positions in the third digital model 300 (and resulting dental mold).

Figure 3A:
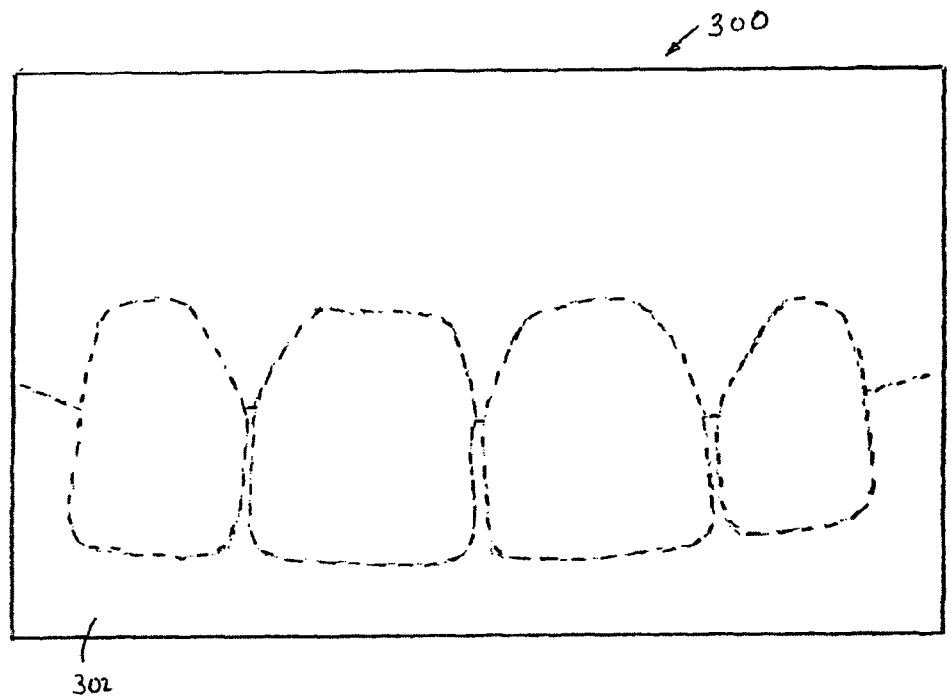
FIGS. 3A-D are illustrations of a negative third digital model 300 showing a solid volume 302 defining a void volume 304 corresponding to a planned dental structure 210. Dotted lines illustrate interior spatial surface contours defined by the solid volume 302 that are not externally visible. (A: front view; B: top view; C: bottom; D: side cross-sectional view through maxillary lateral incisor).
Figure 3B:
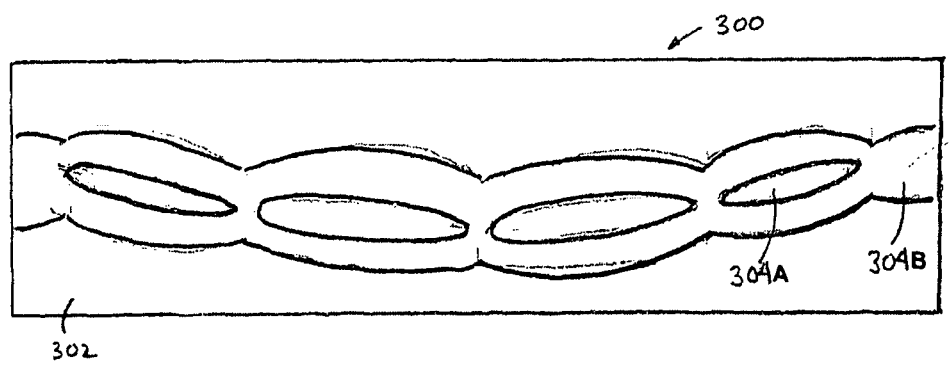
Figure 3C:
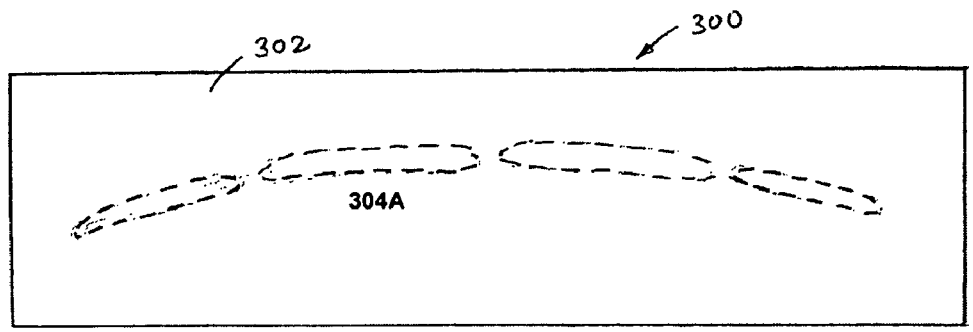
Figure 3D:
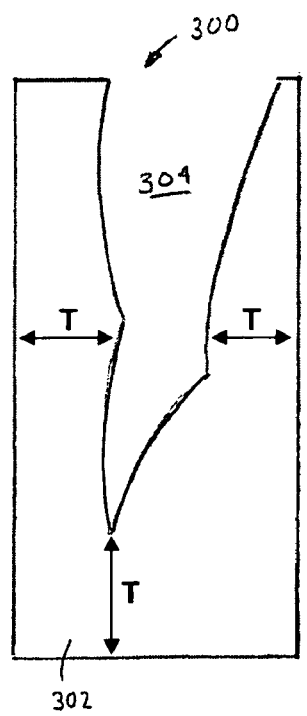

As shown in FIGS. 3A-D, the third digital model 300 includes a solid volume 302 that corresponds to walls (both internal and external) of the eventual dental mold 400. The solid volume 302 defines a void volume 304 that corresponds to the planned dental structure 210. The figures include four views: a front view (FIG. 3A), a top view (FIG. 3B, where "top" represents the portion of the model that fits against a patient's gum in the final mold), a bottom view (FIG. 3C, where "bottom" represents the portion of the model that extends below the patient's teeth in the final mold), and a side cross-sectional view through maxillary lateral incisor 114B (FIG. 3D). In the figures, dotted lines illustrate interior spatial surface contours defined by solid volume 302 that are not externally visible. The void volume 304 generally includes two portions: (a) a relatively narrower tooth portion 304A that represents the portion of the planned dental structure 210 where teeth 114 extend from the gum 112, and (b) a relatively wider gum portion 304B that represents the portion of the planned dental structure 210 corresponding to the patient's gum 112.

The foregoing describes a particular method for arriving at the third digital model 300 as a negative model of the planned dental structure 210, namely: acquisition of positive digital model of the existing dental structure 110, formation of a positive digital model therefrom to represent the planned dental structure 210, and formation of a negative digital model therefrom also to represent the planned dental structure 210. However, the negative third digital model can be obtained in any convenient manner. For example, a negative digital model of the existing dental structure 110 can be directly acquired in the first instance, and the negative digital model can be modified according to known techniques/software to create a digital model of the planned dental structure 210 in a second step. Similarly, a positive digital model of the existing dental structure 110 can be acquired as described above, the positive digital model can then be converted to negative digital model of the existing dental structure 110, and the negative digital model can be modified to create a digital model of the planned dental structure 210. Accordingly, a more general description of the method of mold formation can be expressed as: (a) generating a three-dimensional digital model corresponding to a negative of a planned dental structure; (b) digitally sectioning the digital model into at least one buccal model portion and at least one lingual model portion of the digital model; and (c) creating a dental mold comprising at least one buccal mold portion and at least one lingual mold portion based on the sectioned digital model.

Figure 4A:
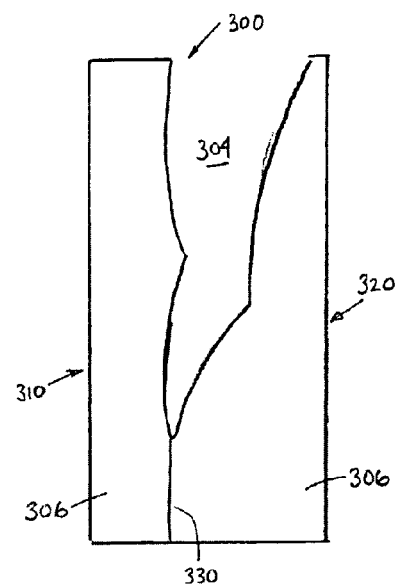
FIGS. 4A-C are illustrations of a digitally sectioned third digital model 300 showing sub-volumes 306 and a common interfacial surface 330 defining a buccal model portion 310, a lingual model portion 320, and a complementary alignment structure 332. (A: side cross-sectional view through maxillary lateral incisor, B: bottom view; C: top view).
Figure 4B:
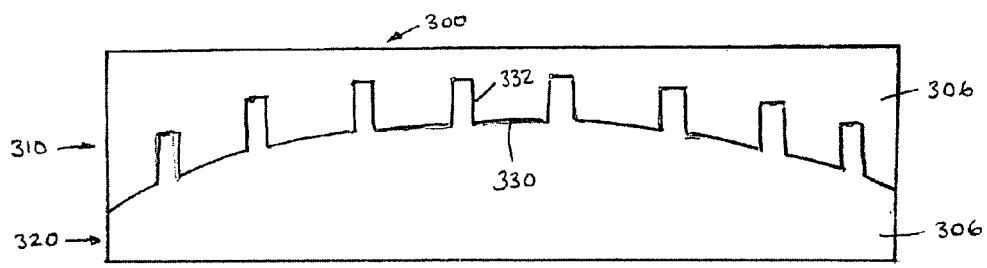
Figure 4C:
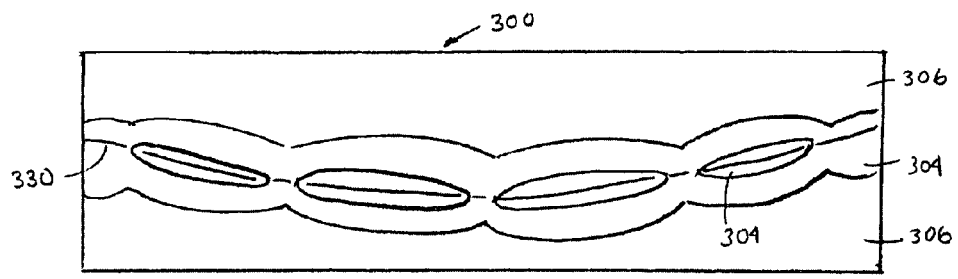

FIGS. 4A-C illustrate the digital sectioning of the third digital model 300 into components that correspond to pieces of the eventual dental mold 400. Sectioning of the third digital model 300 allows unimpeded placement of the corresponding dental mold 400 components over divergent angles and heights of contour of the teeth 114 and gum 112. As shown, the solid volume 302 of the third digital model 300 is partitioned into two or more sub-volumes 306. The particular location of the sectioning is selected to create at least one buccal model portion 310 of the third digital model 300 and at least one lingual model portion 320 of the third digital model 300 from the sub-volumes 306. As a result of the sectioning, the buccal model portion 310 and the lingual model portion 320 share at least one common interfacial surface 330 in the third digital model 310. The location of the sectioning is not particularly limited, but may be conveniently selected to follow a line/surface generally defined by a centerline/leading edge of the teeth 214 in the planned dental structure 210, for example as illustrated in FIGS. 4B, 4C, and 7 by the projected line defined by the common interfacial surface 330.

As shown in FIG. 4B, the common interfacial surface 330 can define one or more complementary alignment structures 332 between the buccal model portion 310 and the lingual model portion 320 of the third digital model 300. The complementary alignment structure 332 can include essentially any irregular or non-planar geometric shape/contour that deviates from the general curvature of the interfacial surface 330 defined by the planned dental structure 210. The irregular common interfacial surface 330 and complementary alignment structure 332 facilitate the proper alignment of the eventual mold portions during assembly of the dental mold 400 and limiting slippage of the mold portions in the assembled dental mold 400. As specifically illustrated in FIG. 4B, the complementary alignment structure 332 can include a plurality of ribs (illustrated on the lingual side) and a plurality of complementary grooves (illustrated on the buccal side). The ribs and grooves ensure that the components of the eventual dental mold 400 are properly aligned when assembled. Further, the ribs and grooves can be machined within a specific tolerance so that they additionally create a frictional force that helps to maintain the dental mold 400 in an assembled configuration once installed in a patient's mouth. The particular shape of the complementary alignment structure 332, however, is not particularly limited and can include other mating shapes such as rods/holes, etc.

As shown in FIGS. 4A-C, the digitally sectioned third digital model 300 includes only one buccal model portion 310 and only one lingual model portion 320. This two-piece configuration can be suitable when only a subset of teeth along a dental arch forms the target of the planned dental restoration. In this case, the limited net curvature of the target area will permit a two-piece dental mold 400 to be formed and assembled in a patient's mouth.

Figure 7:
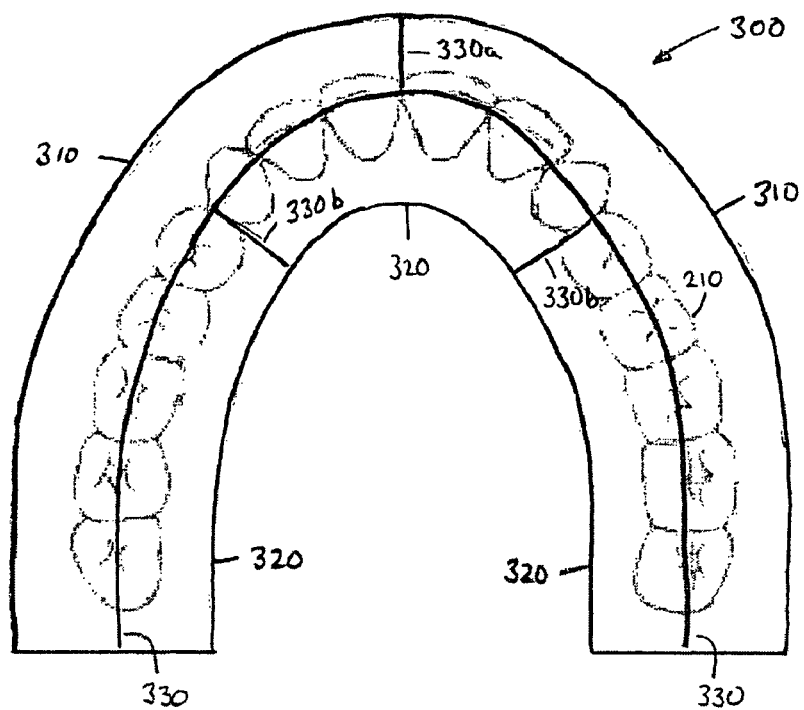
FIG. 7 is an illustration of digitally sectioned third digital model 300 (bottom view) having multiple buccal model portions 310 and lingual model portions 320 with a buccal-lingual common interfacial surface 330, a buccal-buccal common interfacial surface 330a, and a lingual-lingual common interfacial surface 330b. Faint lines illustrate interior spatial surface contours of planned dental structure 210.

As shown in FIG. 7, however, the digitally sectioned third digital model 300 can include multiple buccal model portions 310 and multiple lingual model portions 320. This can be appropriate when (a) the buccal model portions 310 and the lingual model portions 320 together correspond to an entire dental arch of the planned dental structure 210 (e.g., as shown in FIG. 7) and/or (b) when only a subset of teeth along a dental arch forms the target of the planned dental restoration, but the subset involves substantial curvature. In this case, (a) each buccal model portion 310 shares at least one common interfacial surface 330 with at least one lingual model portion 320 in the third digital model 300, (b) each buccal model portion 310 shares at least one common interfacial surface 330A with at least one other buccal model portion 310 in the third digital model 300, (c) each lingual model portion 320 shares at least one common interfacial surface 330 with at least one buccal model portion 310 in the third digital model 300, and (d) each lingual model portion 320 shares at least one common interfacial surface 330B with at least one other lingual model portion 320 in the third digital model 300. Although not shown, the additional interfacial surfaces 330A and 330B can have complementary alignment structures similar to those described for the interfacial surface 330 to facilitate the intra-buccal or intra-lingual mold piece alignment and assembly, respectively. The locations defining the interfaces between adjacent buccal or lingual model portions 310, 320 are not particularly limited, and can be selected as desired to accommodate the curvature of a particular patient's dental structure. As shown in FIG. 7, two buccal model portions 310 can be conveniently divided between the central incisors, and the three lingual model portions 320 can be conveniently divided between the canines and premolars. The overlapping structure shown in FIG. 7 (e.g., where each buccal model portion 310 contacts at least two lingual model portions 320) is desirable, in particular in combination with the complementary alignment structure, to facilitate the alignment and assembly of the multi-part dental mold 400.

Figure 5A:
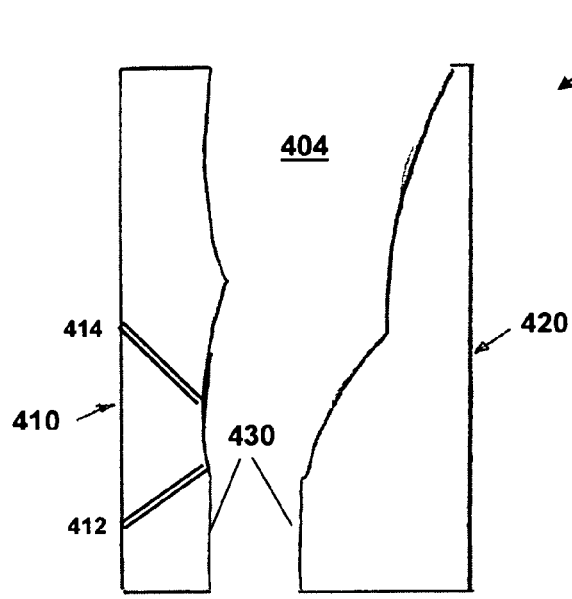
FIGS. 5A-C are illustrations of a dental mold 400 showing a buccal mold portion 410, a lingual mold portion 420, and a common interfacial surface 430 defining a complementary alignment structure 432. (A: side cross-sectional view through maxillary lateral incisor, B: bottom view; C: top view).
Figure 5B:
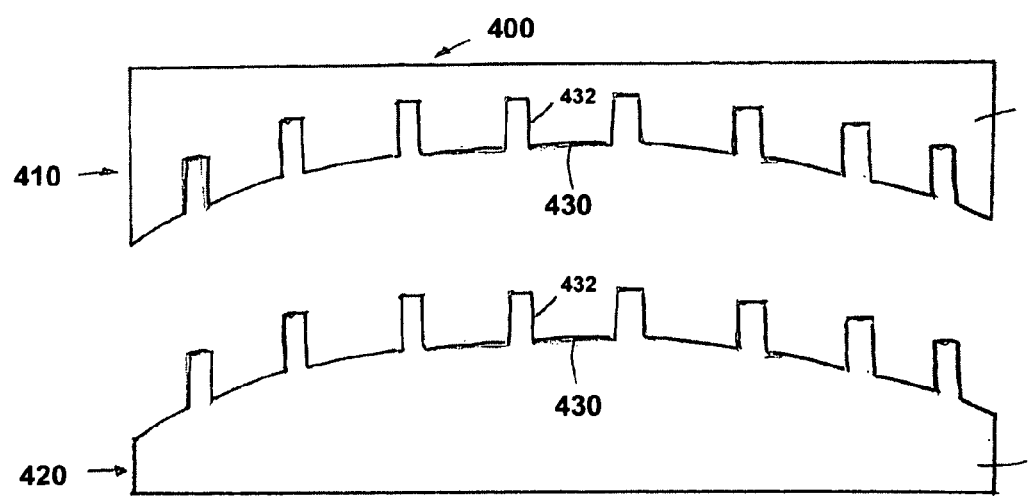
Figures 5C, 6:
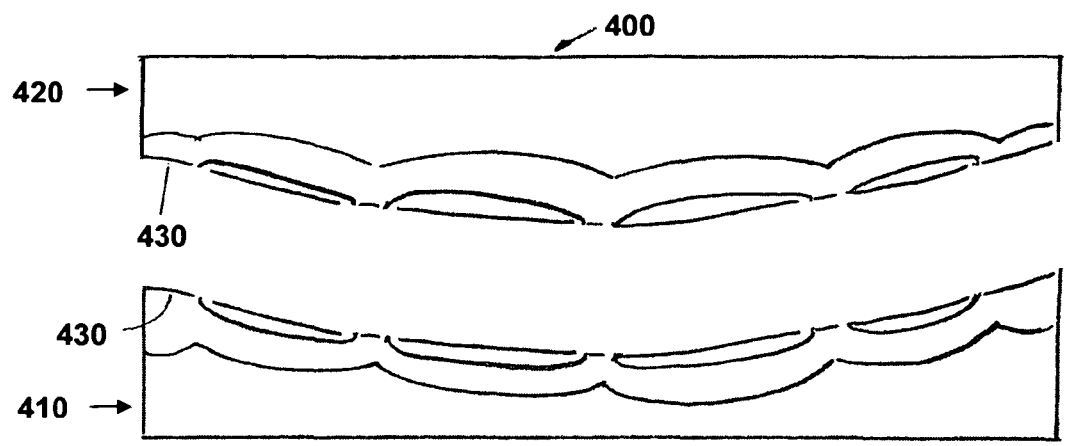
FIG. 6 is an illustration of a system and method for forming a dental mold 400 from a digitally sectioned third digital model 300.

FIGS. 5A-5C illustrate the creation of a physical dental mold 400 once the third digital model 300 has been digitally sectioned into the buccal and lingual model portions 310, 320. The dental mold 400 includes at least one buccal mold portion 410 the has a shape corresponding to the buccal model portion 310 and at least one lingual mold portion 420 that has a shape corresponding to the lingual model portion 420. The buccal and lingual mold portions 410, 420 are separate structures that together define a void volume 404 corresponding to the planned dental structure 210 when assembled (e.g., when aligned and mated at a common interfacial surface 430 that corresponds to the common interfacial surface 330 in the third digital model 300). Analogous to the third digital model 300, the dental mold 400 also can include complementary alignment structure 432 to help align and assemble the dental mold 400 components in a patient's mouth.

The components of the dental mold 400 can be manufactured by any desired method. Suitably, the buccal and lingual mold portions 410, 420 are formed using a computer-aided manufacturing (CAM) system using the three-dimensional digital models of the buccal and lingual model portions 310, 320 as inputs to the CAM system. An example of a suitable CAM method and system is shown in FIG. 6. In the method, the sectioned third digital model 300 is transmitted by the computer system 130 (e.g., as separately transmitted buccal and lingual model portions 310, 320) as instructions to a CAM apparatus 140 (e.g., a computer numerically controlled (CNC) milling machine). A mold blank 142 also is mounted in the CAM apparatus 140 (e.g., onto a substrate holder). A CAM or CNC machining process is then performed by the apparatus 140 to form the buccal or lingual mold portion 410 or 420 according to the given set of machining instructions. The resulting mold portion 410 or 420 is removed from the apparatus 140 and further processed as desired (e.g., to remove extraneous structure remaining from the blank 142 as a result of the machining process, which extraneous structure is not needed to form the mold portion 410 or 420). The machining process is then repeated with additional mold blanks 142 and additional machining instructions corresponding to the buccal or lingual model portions 310 or 320 until all of the buccal and lingual mold portions 410, 420 of the dental mold 400 have been formed. Representative apparatus and methods for performing the CAM/CNC machining process are illustrated in U.S. Pat. No. 7,163,443, and U.S. Pat. No. 7,178,731, incorporated herein by reference. A suitable commercial dental CAM apparatus system is the INLAB MC XL (available from Sirona Dental Systems), which integrates with the CEREC system described above. Another such dental CAM apparatus is the E4D MILLING CENTER (available from D4D Technologies), which integrates with the E4D DENTIST system described above.

The dental mold 400, its component mold portions 410, 420, and the precursor mold blank 142 can be formed from any suitable biocompatible material (e.g., a polymeric material such as a thermoplastic). Suitably, the material is a rigid polymeric material, for example a thermoplastic acrylic polymer such as poly(methylmethacrylate). The material is suitably a transparent material to facilitate the transmission of light (e.g., UV light) that permits the in situ curing of a fluid polymer composition used to perform a dental restoration technique. An example of a non-polymeric material includes transparent porcelain (glass) that can be milled to the fine dimensions appropriate for the dental mold 400. Alternatively or additionally, the material can include a heating element (e.g., an embedded internal metal rod or strip; not shown) that can be used to heat-cure a fluid polymer composition in situ (e.g., either instead of or in addition to light curing through a transparent mold wall).

When the dental mold 400 is to be used in an injection molding dental restoration process (e.g., as subsequently described herein), an inlet port 412 and an outlet port 414 are added to the dental mold 400. As shown in FIG. 5A, the inlet and outlet ports 412, 414 are both positioned in the buccal mold portion 410, but the ports 412, 414 can generally be placed in any convenient location that provides fluid communication to shape/volume that represents the difference between the existing dental structure 110 and the planned dental structure 210. As illustrated, the inlet port 412 and the outlet port 414 are positioned such that, when the dental mold 400 is assembled, the inlet port 412 and the outlet port 414 (i) are in fluid communication with each other via the void volume 440 (FIG. 8) defined by the assembled dental mold 400 and (ii) are individually in fluid communication with a volume external to the assembled dental mold 400 (e.g., the patient's dental cavity). The inlet port 412 is placed in the mold 400 to allow access for a fluid polymer composition to be injected. An outlet port 414 is placed in the mold 400, to allow air to escape as the restorative polymer composition is forced into the void 440 through the access of the inlet port 412. The ports 412, 414 are suitably placed in the mold 400 using an air rotor drill motor handpiece and a bur (e.g., a BRASSELER #849L 009 diamond bur (Savannah, Ga.)).

Figure 9:
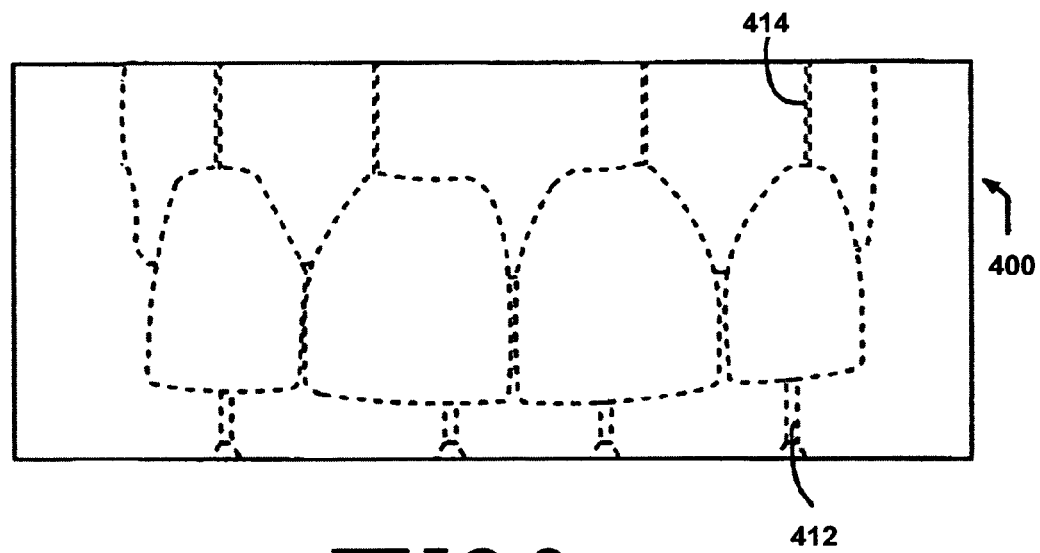
FIG. 9 illustrates the dental mold 400 with inlet and outlet ports 412, 414 adjacent to each of the teeth to be restored.

Typically, at least one inlet port 412 and outlet port 414 are included in the mold 400 for each tooth 112 to be restored (FIG. 9).

Dental Mold Assembly

Figure 8:
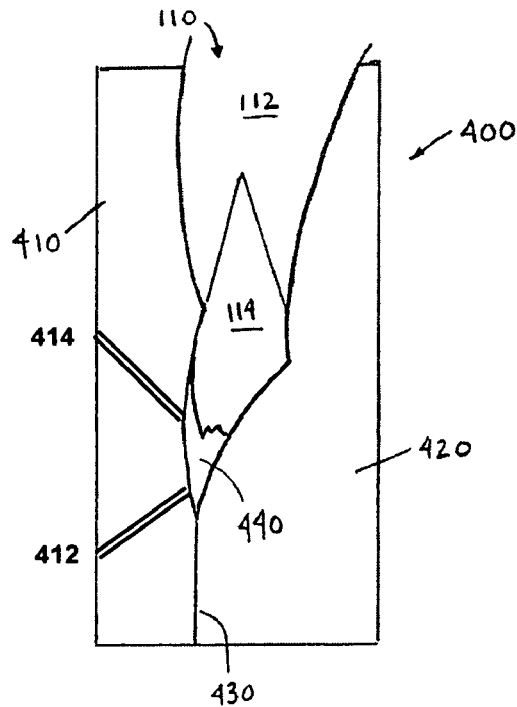
FIG. 8 is an illustration of dental mold 400 in assembled configuration around tooth 114 and gum 112 of existing dental structure 110. A closed space 440 to be filled by a fluid polymer composition for performing a dental restoration is defined by components of dental mold 400 and existing dental structure 110.

The dentist or dental professional now possesses a dental mold 400 that is a negative of the planned dental structure 210. When the mold 400 is assembled over a patient's existing dental structure, it will fit securely and precisely. As shown in FIG. 8, the patient's teeth 114 and gum 112 fill the void volume 404 in the mold 400, except in a closed space 440 which represents the volume difference between the existing dental structure 110 and the planned dental structure 210. The closed space 440 is in fluid communication with the inlet and outlet ports 412, 414 and represents the volume to be filled by a fluid polymer composition in a subsequent dental restoration process.

The dental mold 400 is not generally assembled before being fit over the patient's teeth 114 and gum 112. This is due to the natural curvature, or height of contour, of the patient's existing dental structure 110, which curvature would normally prevent the simple snap-fitting of a rigid, assembled dental mold 400 over the patient's teeth 114 and gum 112. Due to this curvature (e.g., and additionally the rigid nature of the mold 400 material), the dental mold 400 is generally assembled from its component buccal and lingual mold portions 410, 420 directly in the patient's mouth using the following steps: (i) seating at least a portion of the buccal mold portion 410 against a buccal side of the patient's gum 112 or tooth 114, (ii) seating at least a portion of the lingual mold portion 420 against a lingual side of the patient's gum 112 or tooth 114, (iii) contacting the buccal mold portion 410 and the lingual mold portion 420 at their common interfacial surface 430, (iv) securing the buccal mold portion 410 and the lingual mold portion 420 in place. The foregoing steps are repeated until all of the mold 400 components have been assembled (e.g., when there is more than one buccal and/or lingual mold portions 410, 420). The buccal and lingual mold portions 410, 420 can be held in place by any suitable means, for example by fitting a clip (not shown) over adjacent buccal and lingual mold portions 410, 420 and/or by frictional forces between mated complementary alignment structures 432. The resulting assembled the dental mold 400 is in a sealed configuration over the tooth 114 and the gum 112 of the patient, and the sealed configuration define the closed space 440 between the dental mold 400 and the existing dental structure 210 (e.g., the space defined more generally between any combination of the buccal mold portion 410, the lingual mold portion 420, the tooth 114, and/or the gum 112).

Dental Restoration Procedure

The dental mold 400, once formed according to any of the various foregoing embodiments, can be used to perform a dental restoration with a fluid polymer composition on a patient having an existing dental structure in need of dental restoration to a planned dental structure. The method generally includes the steps of (i) preparing selected teeth 114 to be restored for bonding with the fluid polymer composition, (ii) optionally, covering teeth 116 which are not to be restored with a polymer release material 48, (iii) assembling the dental mold 400 over the existing dental structure 210 as described above to define the closed space 440, (iv) injection molding via the inlet port 412 a fluid dental restoration polymer composition which is curable on prepared teeth 114 to be restored into the mold 400 to fill the closed space 440 in the mold 400 with the covered teeth 116 and the teeth 114 to be restored, (v) curing the fluid polymer composition onto the teeth 114 to be restored in the dental mold 400, and (vi) removing the dental mold 400 from the teeth 114 and the polymer release material 48, if present, from the covered teeth 116 to provide the planned dental structure 210 in the patient. A specific application of the foregoing process is described in more detail below.

The patient is prepared according to normal custom. Anti-anxiety agents, and anesthetics are used as needed. The enamel and dentin tooth surfaces are prepared for composite bonding according to standard procedures.

Figure 10:
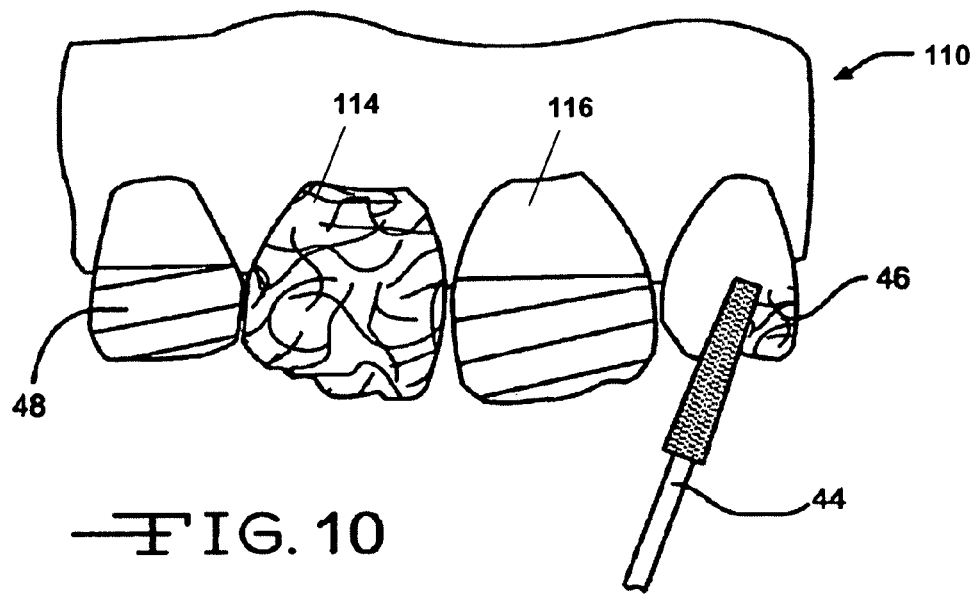
FIG. 10 shows preparation of a patient's teeth 114 by roughening the teeth 114 with a fine diamond bur 44 and covering the teeth 114 with a polymer release material 48.
Figure 11:
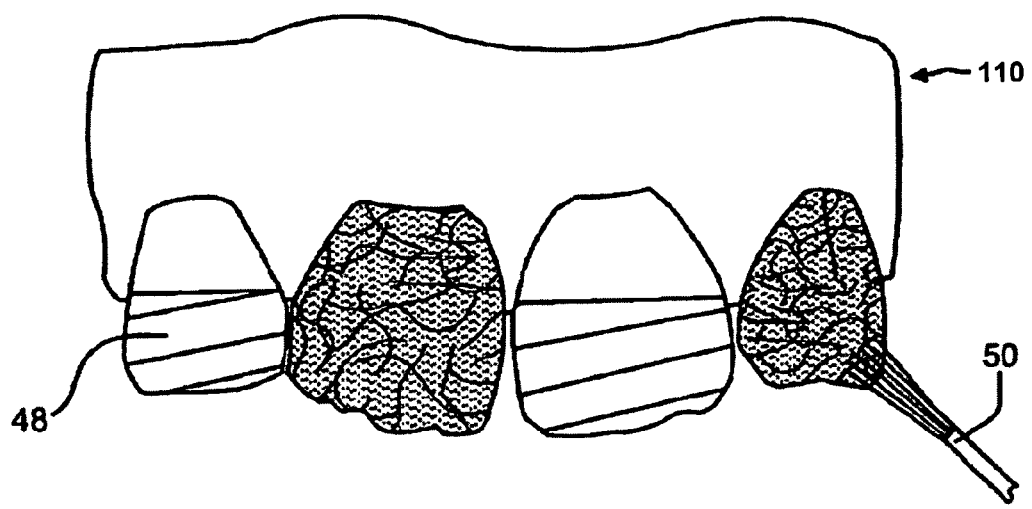
FIG. 11 shows the application of a bonding resin primer after teeth 114 have been etched.
Figure 12:
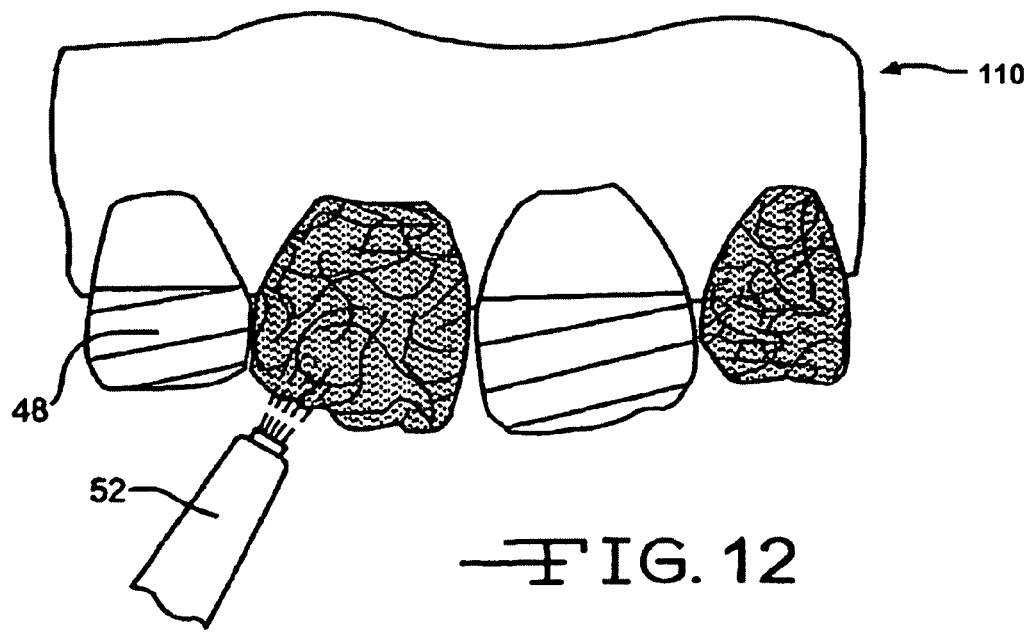
FIG. 12 shows the light curing of a bonding agent applied after the bonding resin primer.

A typical procedure is as follows: The teeth 114 are lightly scuffed 46, or roughened with a fine diamond bur 44 as shown in FIG. 10. These surfaces of the teeth 114 are etched (e.g., with a twenty second application of 35% phosphoric acid gel) and then rinsed with water. The teeth 114 will appear a frosty white color when etched. A thin, non-viscous bonding resin primer is then brushed onto the tooth 114 using brush 50 as shown in FIG. 11. Next, a bonding agent (which is a slightly more viscous resin) is applied and is light 52 cured as shown in FIG. 12. The bonding agent can include any suitable, approved dental bonding agent. In an embodiment, the bonding agent comprises methacrylate ester monomers and the primer comprises alkyl dimethacrylate resins. The primer and bonding agent can be the OPTIBOND FL primer and adhesive (available from Kerr Corporation; Orange, Calif.).

Figure 13:
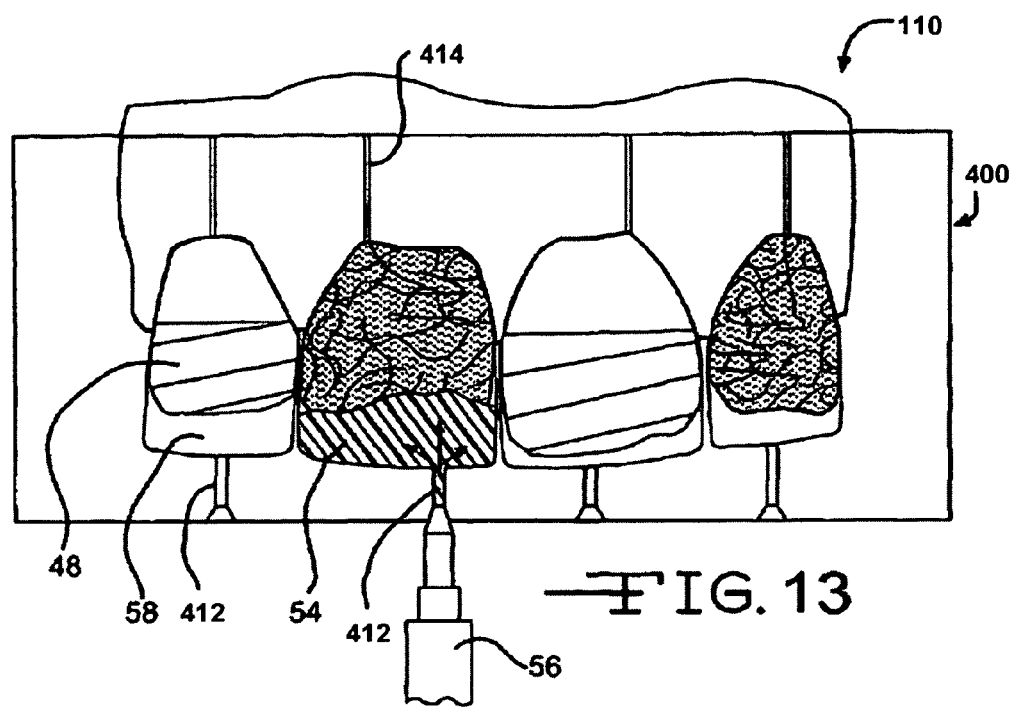
FIG. 13 shows the injection of the flowable composite resin 54 with a syringe 56 having a narrow tip.

One way to restore multiple teeth 114 is to restore every other tooth 114 (i.e., alternating teeth 114) in two separate applications. That way, the teeth 114 are not fused together by the bonding resins. Teeth 116 not to be restored/bonded in the first application are "draped", or isolated by covering with a polymer release material 48 such as a pipe thread tape. The polymer release material 48 can be a poly(tetrafluoroethylene) tape. As such, every other tooth 116 will be covered with a wrap of polymer release material 48. The first teeth 114 to be restored will be not covered. The mold 400 is then assembled over the patient's teeth 114/116 and gum 112. The flowable composite resin 54 is now injected, with moderate pressure from the thumb on the composite syringe 56 plunger. FIG. 13 shows the injection of the flowable composite resin 54 with the syringe 56 having a narrow tip into the inlet port 412 over a tooth 114 to be treated after the mold 400 has been assembled in the patient's mouth. In an alternate embodiment, the polymer release material 48 can be omitted and all teeth can be restored in one step (i.e., with only assembling the mold 400 once in the patient). In this case, polymer that may have flown into and cured within interstitial positions between adjacent teeth 114 can be removed subsequent to disassembly and removal of the mold 400 from the patient (e.g., using a small dental knife or dental saw).

Figure 14:
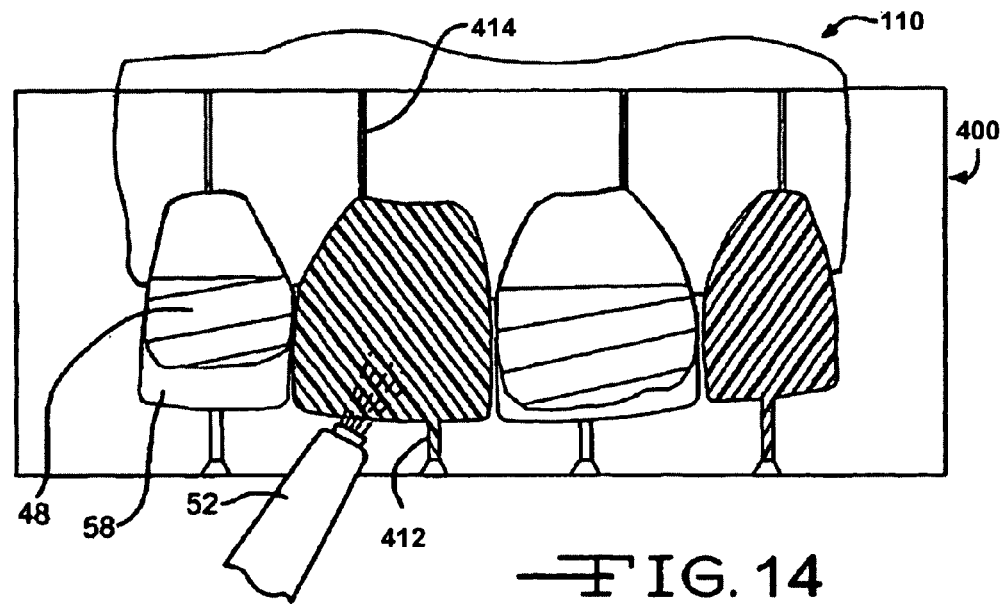
FIG. 14 shows the curing of the flowable composite resin using a curing light 52.

It is preferable to use a flowable composite resin 54 to restore with this technique. Many such materials are available for use. Some examples of composite resins are described in U.S. Pat. No. 6,479,592 to Rheinberger et al., U.S. Patent Application Publication No. 2004/0167246 to Subelka et al., and U.S. Patent Application Publication No. 2003/0069326 to Stangel et al. hereby incorporated herein by reference in their entireties. One suitable material is the HELIOMOLAR flow composite (available from Ivoclar Vivadent; Amherst, N.Y.). The diameter of the syringe tubing closely approximates the diameter of the BRASSELER diamond bur used to make the injection inlet and outlet ports 412, 414. The syringe 56 tip is placed in an inlet port directly over a tooth 114 not covered by the polymer release material 48. The composite resin 54 is flowed, or injected, by pushing on the syringe 56 plunger with the thumb. The dentist can monitor the progress of the composite resin 54 flow, and can stop applying pressure when the composite resin 54 begins to escape from the outlet port 414. After injection the resin is cured or hardened with electromagnetic energy such as light emitted from a curing light 52 (e.g., 465-480 nm) for thirty seconds as shown in FIG. 14.

Figure 15:
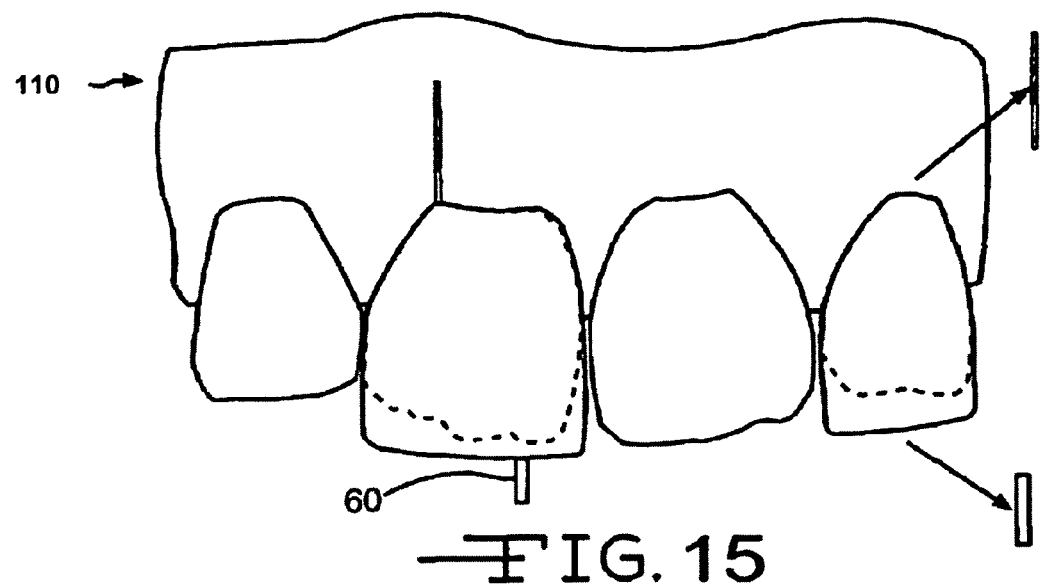
FIG. 15 shows the removal of the dental mold 400, the polymer release material 48, and excess resin 60 prior to smoothing and polishing the restored teeth 114.
Figure 16:
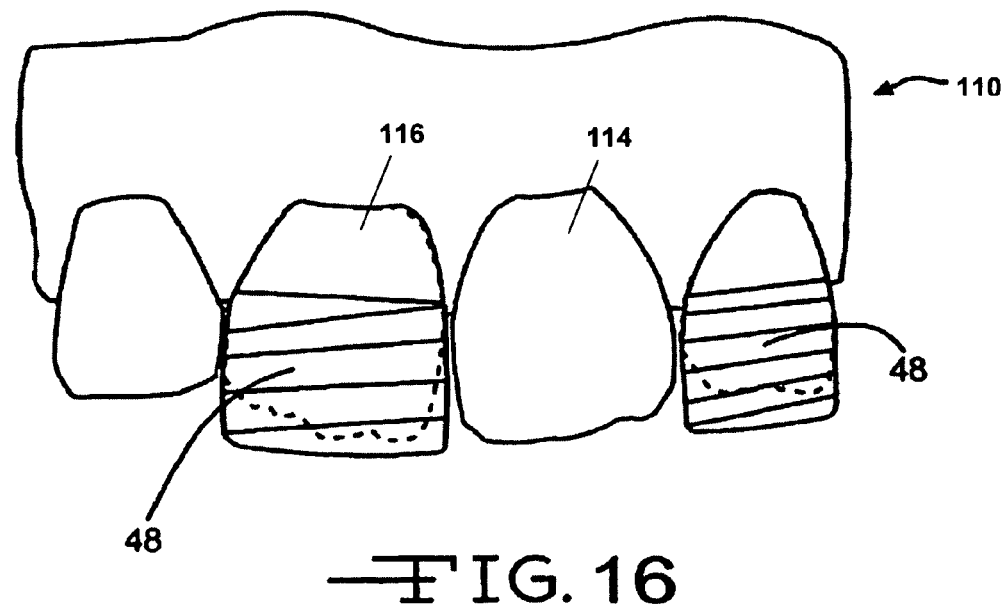
FIG. 16 shows the restored teeth 114 wrapped in the polymer release material 48 in preparation for a second round of dental restoration.

The injection steps illustrated in FIGS. 10-15 are repeated for each tooth that was previously covered by with the polymer release material 48 in the first application. The mold 400 is first disassembled (e.g., by the removal of any retaining means such as clamps and separation of the buccal and lingual mold portions 410, 420 from the patient's dental structure). Next, the polymer release material 48 is removed as well as any excess resin, such as flash 60, as shown in FIG. 15. The restored teeth are smoothed and polished. Polymer release material 48 is then placed over the restored teeth 116. FIG. 16 shows the restored teeth 116 wrapped with the polymer release material 48 in preparation for a second round of restoration similar to the first round shown in FIGS. 10-15. The unrestored teeth 114 previously covered with the polymer release material 48 in FIG. 10 are treated in the second round. Alternating remaining teeth are uncovered, and pre-treated for restoration (e.g., including the etching, priming, bonding steps described above). Next, the mold 400 is reassembled in the patient's mouth, and the composite resin 54 is injected into remaining non-restored tooth 114 spaces followed by a curing process. The mold 400 and the polymer release material 48 are then removed. Afterwards, the remaining restored teeth are finished and polished. Finally, the occlusion (i.e. the bite) of the patient is checked and adjusted if needed.

Because other modifications and changes varied to fit particular operating requirements and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clarity of understanding only, and no unnecessary limitations should be understood therefrom, as modifications within the scope of the disclosure may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Component concentrations expressed as a percent are weight-percent (% w/w), unless otherwise noted. Numerical values and ranges can represent the value/range as stated or an approximate value/range (e.g., modified by the term "about"). Combinations of components are contemplated to include homogeneous and/or heterogeneous mixtures, as would be understood by a person of ordinary skill in the art in view of the foregoing disclosure.

What is claimed is:

1. A method for forming a dental mold, the method comprising:
   (a) scanning an existing dental structure to generate a three-dimensional first digital model of the existing dental structure;
   (b) modifying the first digital model of the existing dental structure to generate a three-dimensional second digital model of a planned dental structure, the planned dental structure having spatial surface contours different from those of the existing dental structure;
   (c) generating a three-dimensional third digital model corresponding to a negative of the second digital model, wherein
      (i) the third digital model comprises a solid volume corresponding to walls of the eventual dental mold, and
      (ii) the solid volume defines a void volume corresponding to the planned dental structure;
   (d) digitally sectioning the solid volume of the third digital model into two or more sub-volumes, thereby defining at least one buccal model portion of the third digital model and at least one lingual model portion of the third digital model such that the buccal model portion and the lingual model portion share at least one common interfacial surface in the third digital model; and
   (e) creating a dental mold comprising at least one buccal mold portion and at least one lingual mold portion, wherein
      (i) the buccal mold portion has a shape corresponding to the buccal model portion;
      (ii) the lingual mold portion has a shape corresponding to the lingual model portion;
      (iii) the buccal mold portion and the lingual mold portion are separate structures that together define a void volume corresponding to the planned dental structure when assembled; and
      (iv) the buccal and mold portions are shaped to engage existing dental structure and adjacent gum tissue.

2. The method of claim 1, further comprising:
   (f) adding at least one inlet port and at least one outlet port to the dental mold such that, when the dental mold is assembled, the inlet port and the outlet port (i) are in fluid communication with each other via the void volume defined by the assembled dental mold and (ii) are individually in fluid communication with a volume external to the assembled dental mold.

3. The method of claim 1, wherein the existing dental structure comprises at least one tooth and neighboring gum portion of a patient in need of dental restoration.

4. The method of claim 3, wherein the existing dental structure comprises an entire dental arch and neighboring gum portion of a patient in need of dental restoration.

5. The method of claim 3, wherein the planned dental structure is consistent with a planned dental restoration procedure selected from the group consisting of fractured tooth repair, decayed tooth repair, worn tooth repair, discolored tooth masking, tooth reshaping, tooth repositioning, tooth rotation, tooth replacement, and combinations thereof.

6. The method of claim 1, wherein the digital sectioning in part (d) comprises defining two or more buccal model portions and two or more lingual model portions of the third digital model such that (i) each buccal model portion shares at least one common interfacial surface with at least one lingual model portion in the third digital model, (ii) each buccal model portion shares at least one common interfacial surface with at least one other buccal model portion in the third digital model, (iii) each lingual model portion shares at least one common interfacial surface with at least one buccal model portion in the third digital model, and (iv) each lingual model portion shares at least one common interfacial surface with at least one other lingual model portion in the third digital model.

7. The method of claim 6, wherein the buccal model portions and the lingual model portions together correspond to an entire dental arch of the planned dental structure.

8. The method of claim 1, wherein the common interfacial surface defines complementary alignment structure between the buccal model portion and the lingual model portion of the third digital model.

9. The method of claim 8, wherein the common interfacial surface comprises an irregular interface for facilitating the proper alignment of the eventual mold portions during assembly of the dental mold and for limiting slippage of the mold portions in the assembled dental mold.

10. The method of claim 8, wherein the complementary alignment structure is selected from the group consisting of rods/holes, ribs/grooves, and combinations thereof.

11. The method of claim 1, wherein the buccal mold portion and the lingual mold portion comprise a transparent polymeric material.

12. The method of claim 11, wherein the transparent polymeric material comprises a thermoplastic acrylic polymer.

13. The method of claim 11, wherein the transparent polymeric material comprises poly(methymethacrylate).

14. The method of claim 1, wherein at least one of the buccal mold portion and the lingual mold portion comprises an internal heating element.

15. The method of claim 1, wherein creating the dental mold in part (e) comprises:
   (i) mounting a mold blank onto a substrate holder of a computer numerically controlled (CNC) machining apparatus;
   (ii) performing a CNC machining process based on the buccal model portion of the third digital model, thereby forming the corresponding buccal mold portion from the mold blank; and
   (iii) repeating parts (i) and (ii) of claim 15 for each of the buccal and lingual model portions in the third digital model, thereby forming each of the corresponding buccal and lingual mold portions of the dental mold.

16. A method for forming a dental mold for a patient having an existing dental structure in need of dental restoration to a planned dental structure, the method comprising:
   (a) providing a three-dimensional digital model corresponding to a negative of a planned dental structure, the planned dental structure having spatial surface contours different from those of an existing dental structure of a patient in need of dental restoration, wherein
      (i) the digital model comprises a solid volume corresponding to walls of the eventual dental mold, and
      (ii) the solid volume defines a void volume corresponding to the planned dental structure;
   (b) digitally sectioning the solid volume of the digital model into two or more sub-volumes, thereby defining at least one buccal model portion of the digital model and at least one lingual model portion of the digital model such that the buccal model portion and the lingual model portion share at least one common interfacial surface in the digital model;
   (c) creating a dental mold comprising at least one buccal mold portion and at least one lingual mold portion, wherein
      (i) the buccal mold portion has a shape corresponding to the buccal model portion;
      (ii) the lingual mold portion has a shape corresponding to the lingual model portion;
      (iii) the buccal mold portion and the lingual mold portion are separate structures that together define a void volume corresponding to the planned dental structure when assembled; and
      (iv) the buccal and mold portions are shaped to engage existing dental structure and adjacent gum tissue.

17. The method of claim 16 further comprising adding at least one inlet port and at least one outlet port to the dental mold such that, when the dental mold is assembled in a mouth of a patient, the inlet port and the outlet port (i) are in fluid communication with each other via the void volume defined by the assembled dental mold and (ii) are individually in fluid communication with a volume external to the assembled dental mold.

* * * * *